United States Patent
Missbach

Patent Number: 5,399,576
Date of Patent: Mar. 21, 1995

[54] THIAZOLES

[75] Inventor: Martin Missbach, Rheinfelden, Switzerland

[73] Assignee: Ciba-Geigy Corporation, Ardsley, N.Y.

[21] Appl. No.: 202,869

[22] Filed: Feb. 25, 1994

Related U.S. Application Data

[63] Continuation of Ser. No. 990,219, Dec. 14, 1992, abandoned.

[30] Foreign Application Priority Data

Dec. 18, 1991 [CH] Switzerland .................. 3750/91

[51] Int. Cl.$^6$ .................. C07D 417/12; A61K 31/425
[52] U.S. Cl. .................................... 514/369; 548/183; 548/184
[58] Field of Search .......................... 548/184; 514/369

[56] References Cited

U.S. PATENT DOCUMENTS

| | | | |
|---|---|---|---|
| 4,697,020 | 9/1987 | Storni et al. | 548/184 |
| 5,137,897 | 8/1992 | Thorwart et al. | 514/365 |

FOREIGN PATENT DOCUMENTS

| | | |
|---|---|---|
| 69784 | 1/1983 | European Pat. Off. . |
| 691154 | 1/1983 | European Pat. Off. . |
| 2632745 | 6/1975 | Germany . |
| 1325061 | 8/1973 | United Kingdom . |

OTHER PUBLICATIONS

Vigorita, et al. "B,3'-Bi-1,3-thiazolidine]-4,4'-dione system" Chemical Abstracts 102(11):18 No. 89678X (1985).

European Patent Office Search, 18 Mar. 1993.

*Primary Examiner*—Robert Gerstl
*Attorney, Agent, or Firm*—Irving M. Fishman; Karen G. Kaiser

[57] ABSTRACT

Novel thiazoles of formula I

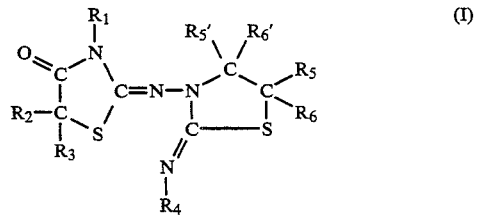

wherein $R_1$ and $R_4$ are lower alkyl, lower alk-2-en-1-yl or lower alk-2-yn-1-yl, $R_2$ and $R_3$ are each independently of the other hydrogen or lower alkyl or together form lower alkylidene, and $R_5$ and $R_6$ are each hydrogen or lower alkyl or together form oxo, and $R_5'$ and $R_6'$ have the same definitions as $R_5$ and $R_6$, with the proviso that at least one of the substituent pairs $R_5$ and $R_6$ or $R_5'$ and $R_6'$ together form oxo, and salts thereof, processes for the preparation of the said compounds, pharmaceutical compositions comprising them and the use thereof as medicinal active ingredients.

11 Claims, No Drawings

THIAZOLES

This is a continuation of Ser. No. 07/990,219, filed Dec. 14, 1992, now abandoned.

The invention relates to novel thiazoles of formula I

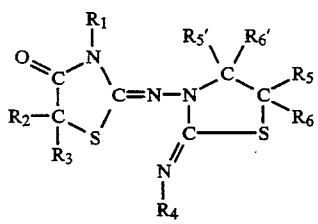

wherein $R_1$ and $R_4$ are lower alkyl, lower alk-2-en-1-yl or lower alk-2-yn-1-yl, $R_2$ and $R_3$ are each independently of the other hydrogen or lower alkyl or together form lower alkylidene, and $R_5$ and $R_6$ are each hydrogen or lower alkyl or together form oxo, and $R_5'$ and $R_6'$ have the same definitions as $R_5$ and $R_6$, with the proviso that at least one of the substituent pairs $R_5$ and $R_6$ or $R_5'$ and $R_6'$ together form oxo, and salts thereof, to processes for the preparation of the said compounds, to pharmaceutical compositions comprising them and to the use thereof as medicinal active ingredients.

Hereinbefore and hereinafter, lower radicals and compounds are to be understood as being, for example, those having up to and including 7, preferably up to and including 4, carbon atoms (C atoms).

Lower alk-2-en-1-yl is, for example, $C_3$–$C_5$alk-2-en-1-yl, such as, especially, allyl or methallyl.

Lower alk-2-yn-1-yl is, for example, $C_3$–$C_5$alk-2-yn-1-yl, such as, especially, prop-2-yn-1-yl or but-2-yn-1-yl.

Lower alkyl is, for example, $C_1$–$C_4$alkyl, such as methyl, ethyl, propyl or butyl.

Lower alkylidene is, for example, $C_1$–$C_4$alkylidene, such as, especially, methylene.

Pharmaceutically acceptable acid addition salts of compounds of formula I are, for example, the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluenesulfonates or N-cyclohexylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, maleinates, fumarates, maleates, tartrates or citrates. Salts of compounds of formula I are, for example, the acid addition salts thereof, for example the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

The compounds of formula I and the pharmaceutically acceptable salts thereof have valuable pharmacological properties. In particular, they exhibit marked anti-arthritic properties. Those properties can be demonstrated in vivo, for example, in the adjuvant arthritis model in rats in accordance with I. Wiesenberg et al., Clin. Exp. Immunol. 78, 245 (1989) in doses of approximately from 0.1 to 0.3 mg/kg and above p.o. or i.p..

The compounds of formula I and the pharmaceutically acceptable salts thereof can therefore be used in the treatment of diseases of the rheumatoid type. Those diseases include, especially, rheumatoid arthritis, juvenile arthritis, ankylosing spondylitis and other seronegative spondylarthritises, for example spondylarthritis in Colitis ulcerosa and Crohn's disease, and also reactive arthritises, collagen diseases, such as Lupus erythematosus, degenerative rheumatic diseases, extra-articular rheumatic and para-rheumatic diseases, for example gout and osteoporosis.

The invention relates especially to compounds of formula I wherein $R_1$ is $C_3$–$C_5$alk-2-en-1-yl or $C_3$–$C_5$alk-2-yn-1-yl and $R_4$ is $C_1$–$C_4$alkyl, $C_3$–$C_5$alk-2-en-1-yl or $C_3$–$C_5$alk-2-yn-1-yl, $R_2$ and $R_3$ are each independently of the other hydrogen or $C_1$–$C_4$alkyl or together form $C_1$–$C_4$alkylidene and $R_5$ and $R_6$, and $R_5'$ and $R_6'$ are each independently of the other hydrogen or $C_1$–$C_4$alkyl or together form oxo, with the proviso that at least one of the substituent pairs $R_5$ and $R_6$ or $R_5'$ and $R_6'$ together form oxo, and salts thereof, especially pharmaceutically acceptable salts thereof.

The invention relates more especially to compounds of formula I wherein the radical $R_1$ is $C_3$–$C_5$alk-2-en-1-yl, such as allyl or methallyl, or $C_3$–$C_5$alk-2-yn-1-yl, such as prop-2-yn-2-yl, and $R_4$ is $C_1$–$C_4$alkyl, such as methyl, or $C_3$–$C_5$alk-2-en-1-yl, such as allyl or methallyl, $R_2$ and $R_3$ are both hydrogen or the same $C_1$–$C_4$alkyl groups, such as methyl, or together form $C_1$–$C_4$alkylidene, such as methylene, and $R_5$ and $R_6$, and $R_5'$ and $R_6'$ are each hydrogen or together form oxo, with the proviso that at least one of the substituent pairs $R_5$ and $R_6$ or $R_5'$ and $R_6'$ together form oxo, and salts thereof, especially pharmaceutically acceptable salts thereof.

The invention relates especially to compounds of formula I wherein $R_1$ is allyl or methallyl, $R_2$ and $R_3$ are both hydrogen or methyl, $R_4$ is methyl, allyl or methallyl and $R_5$ and $R_6$, and $R_5'$ and $R_6'$ are each hydrogen or together form oxo, with the proviso that at least one of the substituent pairs $R_5$ and $R_6$ or $R_5'$ and $R_6'$ together form oxo, and salts thereof, especially pharmaceutically acceptable salts thereof.

The invention relates specifically to the compounds of formula I mentioned in the Examples and salts thereof, especially pharmaceutically acceptable salts thereof.

The process for the preparation of the compounds provided according to the invention is carried out as follows: a compound of formula II

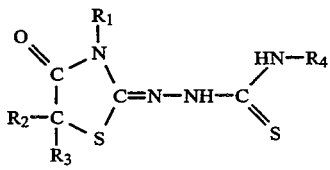

is condensed with a corresponding compound of formula III

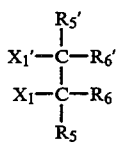

wherein $X_1$ and $X_1'$ are each reactive esterified hydroxy, and $R_5$, $R_6$, $R_5'$ and $R_6'$ are as defined above, in the presence of a basic condensation agent with subsequent heating.

The condensation is effected in the presence of a basic condensation agent, such as a tertiary organic base, such as a tri-lower alkylamine, a Hünig base or an organic nitrogen base, such as pyridine or quinoline, and/or initially with cooling, advantageously in a temperature range of approximately from $+15°$ to $-70°$ C., for example from $0°$ to $-60°$ C., especially from $-40°$ to $-60°$ C., and subsequently with heating to a temperature of from $+20°$ to $+60°$ C., especially from $+30°$ to $+40°$ C.

The compounds of formula II and processes for the preparation thereof, which are based on methods known per se, are known and are described, for example, in GB Patent 1 325 061, U.S. Pat. No. 4,697,020, DE Patent 2 405 395 or DE Patent 2 632 745 as intermediates for the preparation of tumour-inhibiting medicinal active ingredients.

In starting materials of formula III, removable radicals $X_1$ and $X_1'$ that come into consideration are, for example, reactively esterified hydroxy groups, especially halogen, such as chlorine or bromine. Compounds of formula III are known and are, for example, oxalyl chloride or haloacetyl halides, for example bromoacetyl chloride or bromide, which are commercially available.

The condensation of compounds of formula II with compounds of formula III is effected in customary manner, advantageously in an inert solvent, for example an aliphatic halogenated hydrocarbon, such as in dichloromethane, or an aliphatic or cycloaliphatic ether, for example in tetrahydrofuran or dioxane. In a preferred form of process variant a), for example, a compound of formula II is reacted in the presence of triethylamine or pyridine and in dichloromethane or tetrahydrofuran as solvent with a compound of formula III, for example oxalyl chloride or a haloacetyl halide, for example bromoacetyl chloride or bromide, at an initial temperature of from $-40°$ to $-60°$ C. and subsequently the reaction mixture is heated to a temperature of from $+20°$ to $+60°$ C., especially from $+30°$ to $+40°$ C.

The compounds of formula I obtainable by the process according to the invention in the form of an isomeric mixture may, if desired, be separated into the individual isomers, and/or free compounds obtainable in accordance with the invention may be converted into a salt, or a salt obtainable in accordance with the invention may be converted into a free compound or into a different salt.

Compounds obtainable in accordance with the process may be converted in customary manner into different compounds of formula I.

Resulting salts can be convened into the free compounds in a manner known per se, for example by treatment with a base, such as an alkali metal hydroxide, a metal carbonate or hydrogen carbonate, or ammonia, or with another salt-forming base mentioned at the beginning, or with an acid, such as a mineral acid, for example with hydrochloric acid, or with another salt-forming acid mentioned at the beginning.

Resulting salts can be converted into different salts in a manner known per se; for example acid addition salts can be converted by treatment with a suitable metal salt, such as a sodium, barium or silver salt, of a different acid in a suitable solvent in which an inorganic salt being formed is insoluble and is therefore eliminated from the reaction equilibrium, and basic salts can be converted by liberation of the free acid and conversion into a salt again.

The compounds of formula I, including their salts, may also be obtained in the form of hydrates or may include the solvent used for crystallisation.

As a result of the close relationship between the novel compounds in free form and in the form of their salts, hereinbefore and hereinafter any reference to the free compounds and their salts is to be understood as also including the corresponding salts and free compounds, respectively, where appropriate and expedient.

Resulting racemates can also be resolved into the optical antipodes according to known methods, for example by recrystallisation from an optically active solvent, with the aid of microorganisms or by reaction of the resulting diastereoisomeric mixture or racemate with an optically active auxiliary compound, for example in accordance with the acidic, basic or functionally modifiable groups present in compounds of formula I, with an optically active acid, base or an optically active alcohol, to form mixtures of diastereoisomeric salts or functional derivatives, such as esters, and separation thereof into the diastereoisomers from which the desired enantiomer can be freed in the appropriate customary manner. Bases, acids and alcohols suitable for this purpose are, for example, optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluoyltartaric acid, D- or L-malic acid, D- or L-mandelic acid, or D- or L-camphor-sulfonic acid, or optically active alcohols, such as borneol or D- or L-(1-phenyl)ethanol.

The invention relates also to those forms of the process according to which a compound obtainable as intermediate at any stage of the process is used as starting material and the remaining steps are carried out, or a starting material is used in the form of a salt or, especially, is formed under the reaction conditions.

The invention relates also to the novel starting materials that have been developed specifically for the preparation of the compounds according to the invention, especially the group of starting materials that result in the compounds of formula I that are described at the beginning as being preferred, to the processes for their preparation and to their use as intermediates.

The pharmaceutical compositions according to the invention, which comprise the compound according to the invention or a pharmaceutically acceptable salt thereof, are for enteral, such as oral and also rectal, and for parenteral administration to (a) warm-blooded animal(s), the compositions comprising the pharmacological active ingredient on its own or together with a pharmaceutically acceptable carrier. The daily dose of the active ingredient depends upon age and individual condition, and also upon the mode of administration.

The novel pharmaceutical compositions comprise, for example, from approximately 10% to approximately 80% active ingredient, preferably from approximately 20% to approximately 60% active ingredient. Pharmaceutical compositions according to the invention for enteral or parenteral administration are, for example, those in unit dose forms, such as dragées, tablets, capsules or suppositories, and also ampoules. Those compositions are prepared in a manner known per se, for example by means of conventional mixing, granulating, confectioning, dissolving or lyophilising processes. For example, pharmaceutical compositions for oral use can be obtained by combining the active ingredient with solid carriers, optionally granulating a resulting mixture, and, if desired, processing the mixture or granules, if necessary after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatin, tragacanth, methylcellulose and/or polyvinylpyrrolidone, if desired, disintegrators, such as the above-mentioned starches, also carboxymethyl starch, cross-linked polyvinylpyrrolidone, agar, alginic acid or a salt thereof, such as sodium alginate. Excipients are especially flow agents, flow conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical compositions include dry-filled capsules consisting of gelatin, and also soft, sealed capsules consisting of gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycol, to which stabilisers may likewise be added.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycol or higher alkanols. It is also possible to use gelatin rectal capsules that comprise a combination of the active ingredient with a base material. Suitable base materials are, for example, liquid triglycerides, polyethylene glycol or paraffin hydrocarbons.

For parenteral administration there are especially suitable aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran, and, if desired, stabilisers.

The invention relates also to the use of the compounds of formula I, preferably in the form of pharmaceutical compositions. The dose of the active ingredient depends upon the species of warm-blooded animal, its age and individual condition and upon the mode of administration. In normal cases, the approximate daily dose for oral administration to a patient weighing about 75 kg is estimated to be from approximately 5 mg to approximately 1000 mg, especially from approximately 10 mg to approximately 200 mg. That dose can be administered all at once or can be divided into several, for example from 2 to 4, individual doses. Pharmaceutical compositions in unit dose form therefore comprise from approximately 5 mg to approximately 250 mg, especially from approximately 10 mg to approximately 50 mg, active ingredient.

The following Examples serve to illustrate the invention. Temperatures are given in degrees Celsius, pressures in mbar.

EXAMPLE 1

With stirring at $-40°$, 1.9 ml of bromoacetyl bromide are added dropwise over a period of 5 minutes to a mixture of 4.9 g of 3-allyl-thiazolidine-2,4-dione-2-(4-methyl-3-thiosemicarbazone) and 6.2 ml of triethylamine in 100 ml of absolute tetrahydrofuran, and the mixture is stirred at the same temperature for 15 minutes. The suspension is allowed to rise to room temperature and then stirred for 30 minutes at 40°.

After removal of the solvent, the mixture is partitioned between water and methylene chloride. The aqueous phase is extracted a second time and the combined organic phases are dried over sodium sulfate and concentrated. Crystallisation from cold ethanol yields colourless crystals of the compound of formula I in which $R_1$ is allyl; $R_4$ is methyl; $R_2$, $R_3$, $R_5$, and $R_6$ are each hydrogen; and $R_5'$ and $R_6'$ are together oxo, melting point 100°. $^1$H-NMR: 3.15 (s, 3H), 3.9 (2xs, 4H), 4.5 (d, 2H), 5.2–5.4 (m, 2H), 5.95 (m, 1H).

EXAMPLE 2

In a manner analogous to Example 1, starting from 6 g of 3-methallyl-5,5-dimethyl-thiazolidine-2,4-dione-2-(4-allyl-3-thiosemicarbazone) and 4.4 g of bromoacetyl bromide there is obtained, after recrystallisation from ethanol, the compound of formula I in which $R_1$ is methallyl; $R_4$ is allyl; $R_2$ and $R_3$ are each methyl; $R_5$ and $R_6$ are each hydrogen; and $R_5'$ and $R_6'$ are together oxo, melting point 65°. $^1$H-NMR: 1.65 (s, 6H), 1.8 (s, 3H), 3.8 (s, 2H), 3.95 (d, 2H), 4.45 (s, 2H), 4.85 (s, 1H), 4.95 (s, 1H), 5.1–5.25 (m, 2H), 5.9 (m, 1H).

EXAMPLE 3

In a manner analogous to Example 1, starting from 1.7 g of 3-methallyl-5,5-dimethyl-thiazolidine-2,4-dione-2-(4-methyl-3-thiosemicarbazone) and 1.2 g of bromoacetyl bromide there is obtained, after recrystallisation from ethanol, the compound of formula I in which $R_1$ is methallyl; $R_4$ is methyl; $R_2$ and $R_3$ are each methyl; $R_5$ and $R_6$ are each hydrogen; and $R_5'$ and $R_6'$ are together oxo, melting point 135°–138°. $^1$H-NMR: 1.65 (s, 6H), 1.8 (s, 3H), 3.15 (s, 3H), 3.8 (s, 2H), 4.45 (s, 2H), 4.85 (s, 1H), 4.95 (s, 1H).

EXAMPLE 4

In a manner analogous to Example 1, starting from 2.0 g of 3-allylthiazolidine-2,4-dione-2-(4-allyl-3-thiosemicarbazone) and 0.72 ml of bromoacetyl bromide there is obtained, after recrystallisation from ethanol, the compound of formula I in which $R_1$ is allyl; $R_4$ is allyl; $R_2$, $R_3$, $R_5$, and $R_6$ are each hydrogen; and $R_5'$ and $R_6'$ are together oxo, melting point 113°–114°. $^1$H-NMR: 3.85 (s, 4H), 3.95 (d, 2H), 4.5 (d, 2H), 5.1 (d, 1H), 5.15-5.3 (d, 2H), 5.35 (d, 1H) 5.85–6.0 (m, 2H).

EXAMPLE 5

In a manner analogous to Example 1, starting from 1.5 g of 3-propylthiazolidine-2,4-dione-2-(4-methyl-3-thiosemicarbazone) and 0.55 ml of bromoacetyl bromide there is obtained, after recrystallisation from ethanol, the compound of formula I in which $R_1$ is propyl; $R_4$ is methyl; $R_2$, $R_3$, $R_5$, and $R_6$ are each hydrogen; and $R_5'$ and $R_6'$ are together oxo, melting point 109°–111°. $^1$H-NMR: 0.95 (t, 3H), 1.8 (dq, 2H), 3.15 (s, 3H), 3.8–3.9 (m, 6H).

EXAMPLE 6

Tablets, each comprising 10 mg of a compound of formula I, can be prepared as follows:

| Composition (10 000 tablets) | |
| --- | --- |
| active ingredient | 100.0 g |
| lactose | 450.0 g |
| potato starch | 350.0 g |
| gelatin | 10.0 g |
| talc | 60.0 g |
| magnesium stearate | 10.0 g |
| silicon dioxide (highly disperse) | 20.0 g |
| ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 100.0 mg and comprising 50.0 mg of active ingredient; if desired the tablets may be provided with dividing notches for finer adaptation of the dose.

EXAMPLE 7

Hard gelatin capsules, each comprising 20 mg of a compound of formula I, can be prepared, for example, as follows:

| Composition (for 1000 capsules) | |
| --- | --- |
| active ingredient | 20.0 g |
| lactose | 240.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh size and then the microcrystalline cellulose is added through a sieve of 0.9 mm mesh size. The mixture is then again intimately mixed for 10 minutes. Finally, the magnesium stearate is added through a sieve of 0.8 mm mesh size. After mixing for a further 3 minutes, 300 mg portions of the resulting formulation are introduced into size 0 hard gelatin capsules.

EXAMPLE 8

Hard gelatin capsules, each comprising 100 mg of a compound of formula I, can be prepared, for example, as follows:

| Composition (for 1000 capsules) | |
| --- | --- |
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh size and then the microcrystalline cellulose is added through a sieve of 0.9 mm mesh size. The mixture is then again intimately mixed for 10 minutes. Finally, the magnesium stearate is added through a sieve of 0.8 mm mesh size. After mixing for a further 3 minutes, 390 mg portions of the resulting formulation are introduced into size 0 hard gelatin capsules.

EXAMPLE 9

Film-coated tablets, each comprising 50 mg of a compound of formula I, can be prepared as follows:

| Composition (for 1000 film-coated tablets) | |
| --- | --- |
| active ingredient | 50.0 g |
| lactose | 100.0 g |
| corn starch | 70.0 g |
| talc | 10.0 g |
| calcium stearate | 2.0 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed together and moistened with a paste prepared from 15 g of corn starch and water (with heating), and granulated. The granules are dried and the remainder of the corn starch, the talc and the calcium stearate are added and mixed with the granules. The mixture is compressed to form tablets (weight: 240 mg) which are then film-coated with a solution of the hydroxypropylmethylcellulose and the shellac in methylene chloride; final weight of the film-coated tablet: 283 mg.

EXAMPLE 10

A 0.2% injection or infusion solution of a compound of formula I can be prepared, for example, as follows:

| Composition (for 1000 ampoules) | |
| --- | --- |
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added and the mixture is made up to 2500 ml with water. For the preparation of unit dose forms, 1.0 ml or 2.5 ml portions are introduced into glass ampoules which then comprise 2.0 mg or 5.0 mg of active ingredient, respectively.

EXAMPLE 11

An ointment (O/W emulsion) comprising 1% of a compound of formula I and having the following composition:

| active ingredient | 1.0 g |
| --- | --- |
| cetyl alcohol | 3.0 g |
| glycerol | 6.0 g |
| methylparaben | 0.18 g |
| propylparaben | 0.05 g |
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water q.s. ad | 100.0 g |

EXAMPLE 12

A 1% gel comprising a compound of formula I as active ingredient and having the following composition:

| active ingredient | 1.0 g |
| --- | --- |
| Carbopol 934 P | 1.0 g |
| glycerol | 3.0 g |
| isopropanol | 25.0 g |
| Softigen ® 767 | 0.2 g |
| demin. water q.s. ad | 100.0 g |

What is claimed is:

1. A compound of formula I $$\text{(I)}$$

wherein
 $R_1$ and $R_4$ are lower alkyl, lower alk-2-en-1-yl or lower alk-2-yn-1-yl,
 $R_2$ and $R_3$ are each independently of the other hydrogen or lower alkyl or together form lower alkylidene,
 $R_5$ and $R_6$ are each hydrogen or lower alkyl, and
 $R_5'$ and $R_6'$ together form oxo,
or a salt thereof.

2. A compound according to claim 1 of formula I, wherein
 $R_1$ is $C_3$-$C_5$alk-2-en-1-yl or $C_3$-$C_5$alk-2-yn-1-yl and
 $R_4$ is $C_1$-$C_4$alkyl, $C_3$-$C_5$alk-2-en-1-yl or $C_3$-$C_5$alk-2-yn-1-yl,
 $R_2$ and $R_3$ are each independently of the other hydrogen or $C_1$-$C_4$alkyl or together form $C_1$-$C_4$alkylidene
 $R_5$ and $R_6$ are each hydrogen or $C_1$-$C_4$alkyl, and
 $R_5'$ and $R_6'$ together form oxo,
or a salt thereof.

3. A compound according to claim 1 of formula I wherein the radical $R_1$ is $C_3$-$C_5$alk-2-en-1-yl, or $C_3$-$C_5$alk-2-yn-1-yl, and
 $R_4$ is $C_1$-$C_4$alkyl, or $C_3$-$C_5$alk-2-en-1-yl,
 $R_2$ and $R_3$ are both hydrogen or the same $C_1$-$C_4$alkyl groups, or together form $C_1$-$C_4$alkylidene,
 $R_5$ and $R_6$ are each hydrogen, and
 $R_5'$ and $R_6'$ together form oxo,
or a pharmaceutically acceptable salt thereof.

4. A compound according to claim 1 of formula I wherein
 $R_1$ is allyl or methallyl,
 $R_2$ and $R_3$ are both hydrogen or methyl,
 $R_4$ is methyl, allyl or methallyl,
 $R_5$ and $R_6$ are each hydrogen, and
 $R_5'$ and $R_6'$ together form oxo,
or a pharmaceutically acceptable salt thereof.

5. The compound of claim 1 in which $R_1$ is allyl; $R_2$ and $R_3$ are each hydrogen; $R_4$ is methyl; $R_5$ and $R_6$ are each hydrogen; and $R_5'$ and $R_6'$ are together oxo; or a pharmaceutically acceptable salt thereof.

6. The compound of claim 1 in which $R_1$ is methallyl; $R_2$ and $R_3$ are each methyl; $R_4$ is allyl; $R_5$ and $R_6$ are each hydrogen; and $R_5'$ and $R_6'$ are together oxo; or a pharmaceutically acceptable salt thereof.

7. The compound of claim 1 in which $R_1$ is methallyl; $R_2$ and $R_3$ are each methyl; $R_4$ is methyl; $R_5$ and $R_6$ are each hydrogen; and $R_5'$ and $R_6'$ are together oxo; or a pharmaceutically acceptable salt thereof.

8. The compound of claim 1 in which $R_1$ is allyl; $R_2$ and $R_3$ are each hydrogen; $R_4$ is allyl; $R_5$ and $R_6$ are each hydrogen; and $R_5'$ and $R_6'$ are together oxo; or a pharmaceutically acceptable salt thereof.

9. The compound of claim 1 in which $R_1$ is propyl; $R_2$ and $R_3$ are each hydrogen; $R_4$ is methyl; $R_5$ and $R_6$ are each hydrogen; and $R_5'$ and $R_6'$ are together oxo; or a pharmaceutically acceptable salt thereof.

10. A pharmaceutical composition comprising as pharmaceutical active ingredient an anti-rheumatoid effective amount of a compound according to claim 1, in free form or in the form of a pharmaceutically acceptable salt, together with customary pharmaceutical excipients.

11. A method of treating a rheumatoid disease in a animal in need thereof comprising administering to said animal an anti-rheumatoid effective amount of a compound according to claim 1 or a pharmaceutically acceptable salt thereof.

* * * * *